(12) United States Patent
Springhorn (10) Patent No.: US 6,627,059 B2
(45) Date of Patent: Sep. 30, 2003

(54) ELECTROCHEMICAL SENSOR (75) Inventor: Carsten Springhorn, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 80 days.

(21) Appl. No.: 09/815,539

(22) Filed: Mar. 22, 2001

(65) Prior Publication Data

US 2001/0047939 A1 Dec. 6, 2001

(30) Foreign Application Priority Data

Mar. 25, 2000 (DE) .......................... 100 14 995

(51) Int. Cl.[7] .............................. G01N 27/407
(52) U.S. Cl. ................. 204/424; 204/408; 204/426; 204/427
(58) Field of Search ............... 204/421–429, 204/408; 333/243

(56) References Cited

U.S. PATENT DOCUMENTS

| | | | |
|---|---|---|---|
| 2,614,172 A | * | 10/1952 | Greenfield et al. |
| 4,839,019 A | * | 6/1989 | Takahama et al. |
| 6,045,673 A | * | 4/2000 | Kato et al. |
| 6,270,639 B1 | * | 8/2001 | Lenfers et al. |

FOREIGN PATENT DOCUMENTS

| | | | |
|---|---|---|---|
| DE | 198 57 468 | | 6/2000 |
| EP | 0125069 | * | 6/1988 |
| GB | 667471 | * | 3/1952 |

OTHER PUBLICATIONS

Wiedenmann et al., "Exhaust Gas Sensors", Automotive Electronics Handbook, Chapter 6, 1994 month unavailable.

* cited by examiner

Primary Examiner—T. Tung
(74) Attorney, Agent, or Firm—Kenyon & Kenyon (57) ABSTRACT

An electrochemical measuring sensor for determining gas components and/or gas concentrations in gas mixtures, having a sensor element which has at least one signal-forming electrode having a supply lead of the signal-forming electrode and at least one electrical element whose electrical potential differs from the electrical potential of the supply lead of the signal-forming electrode. The supply lead of the signal-forming electrode is at least regionally surrounded by an electrically conducting shielding, so that fault currents appearing because of the potential difference between the supply lead of the signal-forming electrode and the electrical element flow at least predominantly between the electrical element and the shielding.

32 Claims, 6 Drawing Sheets

ELECTROCHEMICAL SENSOR

FIELD OF THE INVENTION

The present invention relates to an electrochemical sensor.

BACKGROUND INFORMATION

Electrochemical sensors are described, for example, in the Automotive Electronics Handbook (1994), chapter 6, Wiedenmann et al., "Exhaust Gas Sensors", for application in exhaust gas analysis of internal combustion engines. Such sensors include a sensor element having at least one signal forming electrode, in which, because of the sensitive properties of the sensor element, a current flows which can be used to determine the concentration of at least one exhaust gas component. Furthermore, the sensor element has at least one electrical element, such as a heater or another electrode, whose potential is clearly different from that of the signal-forming electrode and which is separated from a supply lead of the signal-forming electrode by an insulating layer or an insulating body, for instance a solid electrolyte layer.

The disadvantage of the known sensor is that a fault current into the supply lead of the signal-forming electrode can occur, when the insulating effect of the insulating layer or the insulating body is insufficient because of the potential difference between the signal-forming electrode and the electrical heating element, whereby the measuring signal is corrupted.

To avoid the influence of fault currents into the supply lead of the signal-forming electrode, it was suggested in German Patent Application No. 198 57 468.1 that an electron-conducting intermediate layer be provided between the heater and the signal-building electrode. In this connection, the electron-conducting intermediate layer does not completely separate the heating element from the signal-forming electrode, so that the fault current can be only partially drained off via the electron-conducting intermediate layer. Fault currents can also arise from further electrical elements, which also have a non-neglectable potential difference from the signal-forming electrode, and which are positioned, for example, between the electron-conducting intermediate layer and the signal-forming electrode.

SUMMARY OF THE INVENTION

Compared to the related art, the electrochemical sensor of the present invention has the advantage, that fault currents occurring in the sensor are absorbed by shielding. Thus, the current flowing in the supply lead of the signal-forming electrode, by which the concentration of an exhaust gas component is determined, is not corrupted, making a more precise and uniform functioning of the sensor possible.

The present invention achieves that fault currents flowing in or on the sensor element into the supply lead of the signal-forming electrode can be reduced or avoided by having the fault currents drain off via the shielding.

According to the present invention, it is achieved that at least the predominant part of the fault currents on or in a bonding device which electrically connects the supply lead of the signal-forming electrode via a first conductor element, and the electrical element via a second conductor element by way of at least one cable proceeding from the sensor, are drained off via a shielding printed circuit trace provided on or in the bonding device.

Since the signal-forming electrode and the shielding are at an at least similar potential, it is also achieved that zero or only low currents can flow between the shielding and the signal-forming electrode, even in the presence of an otherwise insufficient insulation between the signal-forming electrode and the shielding.

If the shielding is at an at least close to constant potential, then a possibly appearing low fault current into the signal-forming electrode is at least nearly constant, and therefore easy to correct by an outer protective circuit.

An additional advantage accrues if the shielding is short-circuited with a further electrode which does not take part in the determination of the concentration of the gas component by a current flowing in it, and whose potential lies at least close to the potential of the signal-forming electrode. This has the positive effect that bonding of the shielding can be done away with in the connecting side region of the sensor element.

Because the shielding forms a supply lead of the further electrode, the printing step for the supply lead of the further electrode can also be eliminated.

DETAILED DESCRIPTION

Figure 1:
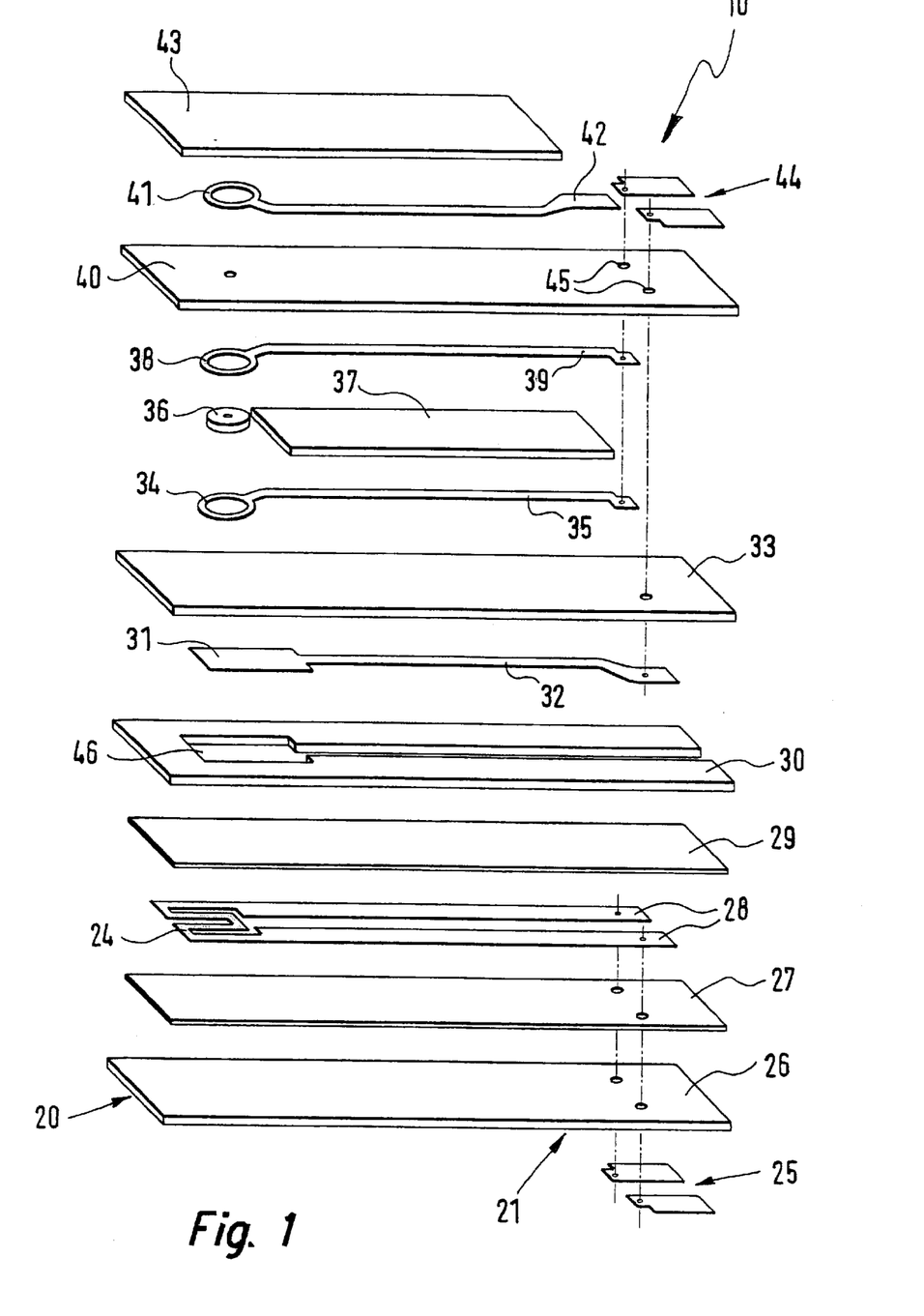
FIG. 1 shows a specific embodiment of a sensor element according to the related art in an exploded diagram.

FIG. 1 shows an exemplary embodiment of an electrochemical sensor, equivalent to the related art, for the analysis of gases, known to one skilled in the art under the name of broadband lambda sensor. The electrochemical sensor contains a planar sensor probe 10 having a region 20 on the measuring side and a region 21 on the connecting side. The sensor element 10 has heater bonding areas 25, a solid electrolyte foil marked as heater foil 26, a heater insulating layer 27, a heater 24 having two supply leads 28, and a further heater insulating layer 29. Furthermore, sensor element 10 contains an additional solid electrolyte foil designated as reference gas channel foil 30, in which a reference gas channel 46 is formed, which is in contact with the air as reference gas atmosphere through an opening in the region of the connecting side 21, as well as a first electrode designated as reference electrode 31 having a reference electrode supply lead 32. Sensor element 10 also has a further solid electrolyte foil designated as measuring foil 33, above reference electrode 31 and reference electrode supply lead 32, as well as a second electrode designated as measuring electrode 34, having a measuring electrode supply lead 35. In addition, the sensor element has a filler layer 37 to form a space not further identified for receiving diffusion barrier 36, a third electrode designated as inner pump electrode 38 having inner pump electrode supply lead 39, another solid electrolyte foil designated as pump foil 40, a fourth electrolde designated as outer pump electrode 41, having outer pump electrode supply lead 42, as well as an outer pump electrode cover 43. In the connecting side region 21 of sensor element 10, the reference electrode 31, the measuring electrode 34 and the inner pump electrode 38 are electrically connected to electrode bonding surfaces 44, present on the outside of sensor element 10, by through-hole platings 45, reference electrode 34 and inner pump electrode 38 being connected to the same bonding surface. In the same way, heater 24 is conducted to the heater bonding surfaces 25 by through-hole plating.

Figure 2:
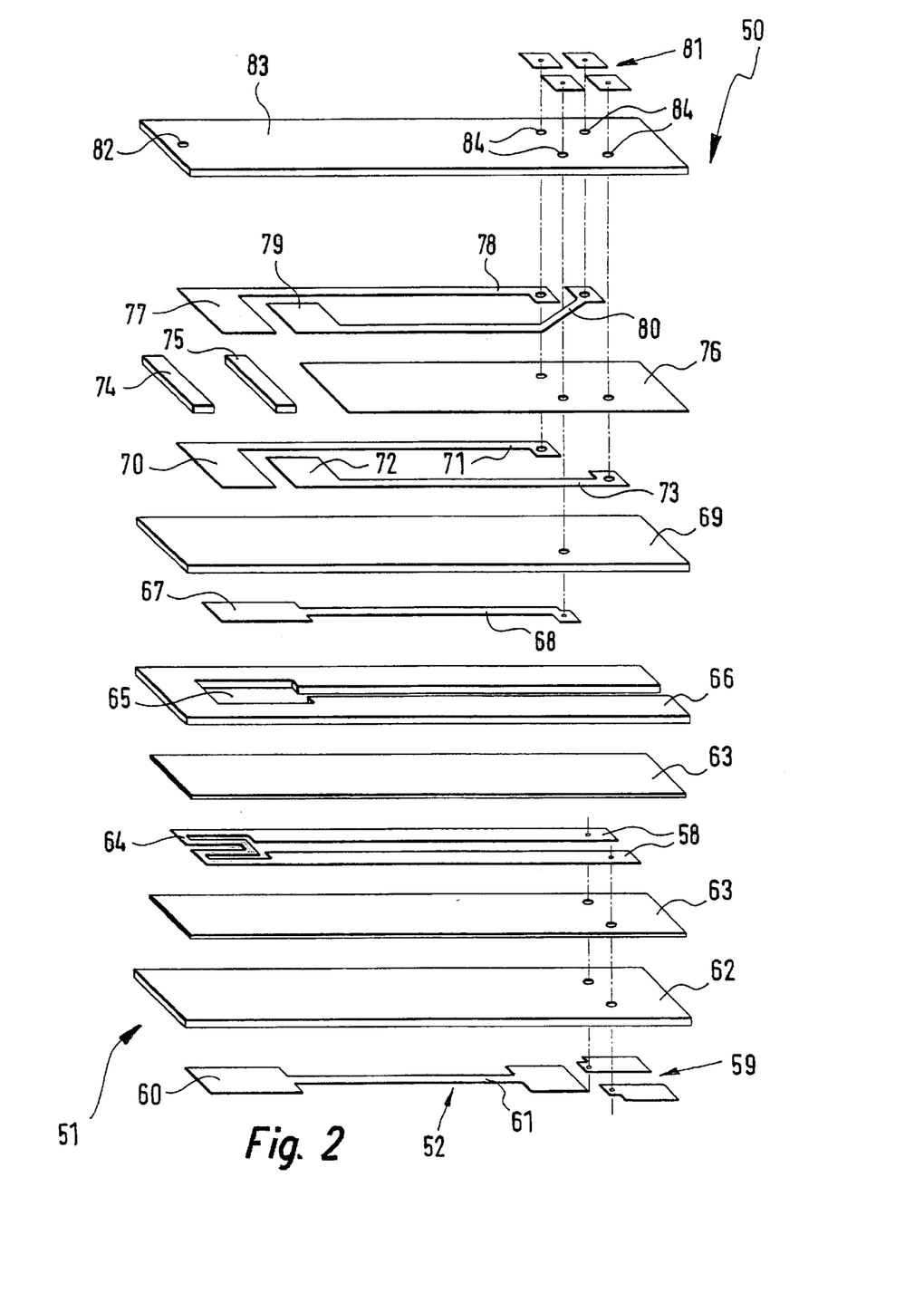
FIG. 2 shows a further specific embodiment of the sensor element according to the related art in an exploded diagram.

FIG. 2 shows a further exemplary embodiment of an electrochemical sensor, equivalent to the related art, for the analysis of gases, corresponding to a NOx sensor. The electrochemical sensor contains a planar sensor element 50 having a measuring side region 51 and a connecting side region 52. The sensor element 50 contains a first electrode designated as oxygen outside pump electrode 60, having a supply lead 61, a solid electrolyte foil designated as heater foil 62, a heater 64, surrounded by two heater insulation layers 63, having two heater supply leads 58, as well as contact surfaces 59 for the oxygen outside pump electrode 60 and the heater 64. Furthermore, sensor element 50 contains an additional solid electrolyte foil designated as reference gas channel foil 66, in which a reference gas channel 65 is formed, which is in contact with the air as reference gas atmosphere via an opening, as well as a second electrode designated as reference electrode 67 having a reference electrode supply lead 68 and another solid electrolyte foil designated as measuring foil 69. Between measuring foil 69 and an additional solid electrolyte foil designated as outer foil 83, in the measuring side region 51 of sensor element 50, between a first and a second diffusion barrier 74, 75 there is a first space designated as pump chamber, and between the second diffusion barrier 75 and the intermediate layer 76 there is a second space designated as measuring chamber.

Figure 3:
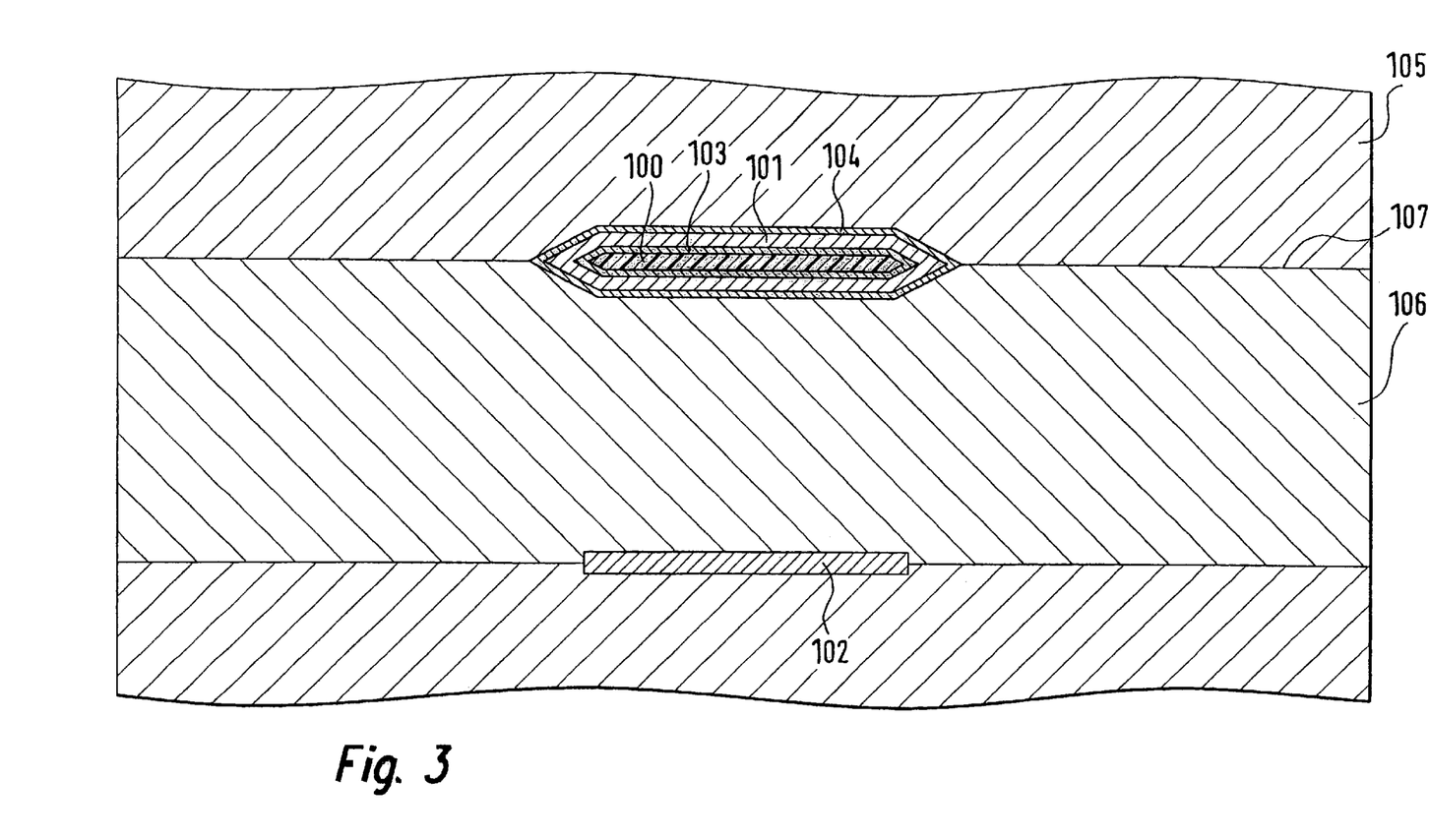
FIG. 3 shows a section through the sensor element according to the present invention, perpendicular to its longitudinal axis in the region of the supply lead.

FIG. 3 shows as exemplary embodiment of the present invention a supply lead 100 of a signal-forming electrode in a border plane 107 between a first and second solid electrolyte layer 105, 106. The supply lead 100 of the signal-forming electrode is enclosed at least to the farthest continuing extent by electrically conducting shielding 101. The supply lead 100 of the signal-forming electrode and the shielding 101 are separated by a first insulating layer 103 and are thereby electrically insulated. A second insulating layer 104 separates the shielding 101 from the solid electrolyte layers 105, 106, which surround it.

Because of external wiring, the shielding 101 has a low potential difference, or none at all, with the supply lead 100 of the signal-forming electrode. The shielding 101 absorbs the fault currents which are produced by a sufficiently large potential difference between supply lead 100 of the signal-forming electrode or the shielding 101 of an electrical element 102, the electrical element 102 being the heater 24, 64 of the sensor element 10, 50 in the present exemplary embodiment.

Figure 4:
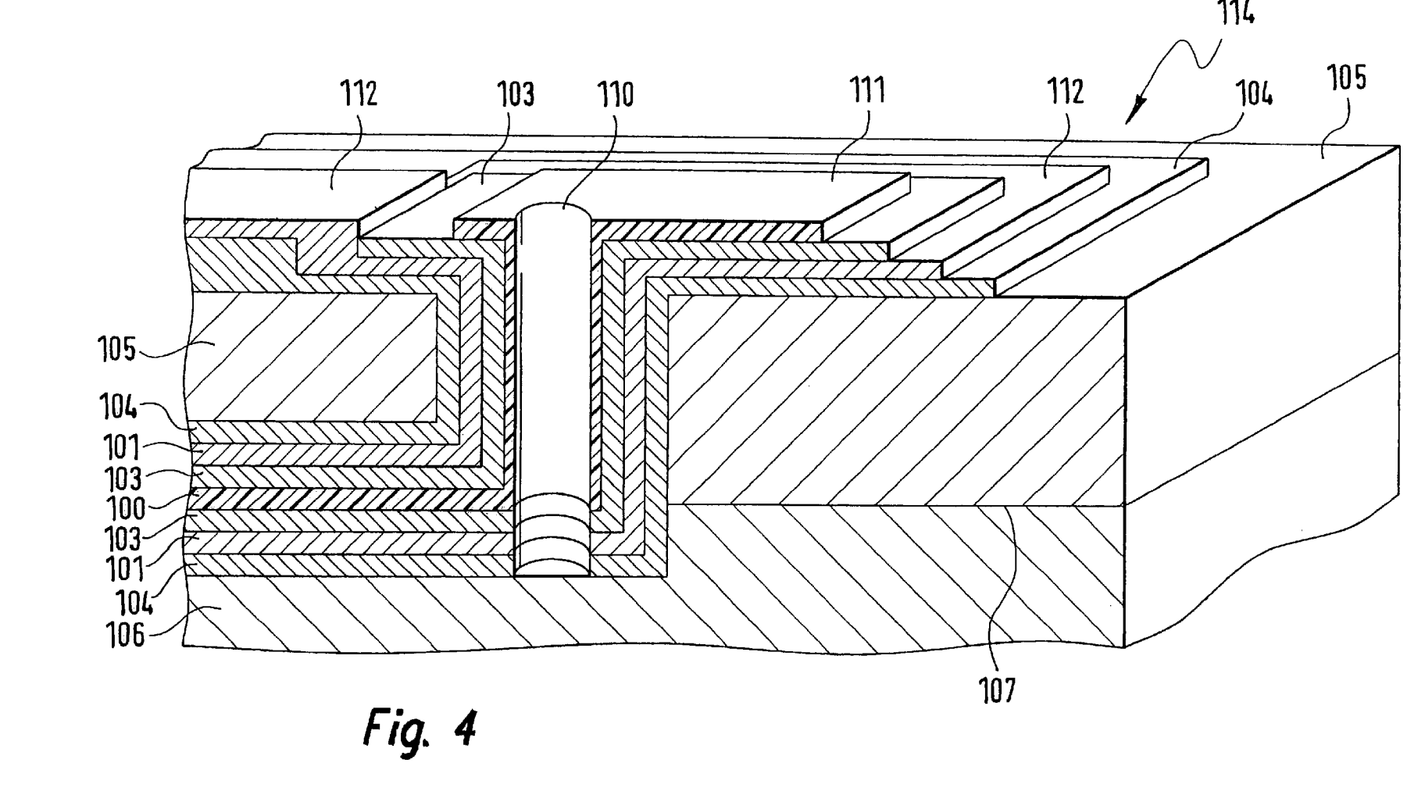
FIG. 4 shows a section through the sensor element according to the present invention in the region of the connecting side along line IV—IV in FIG. 5.

FIG. 4 shows the supply lead of the signal-forming electrode in the connecting side region of a sensor element 114. The supply lead 100 of the signal-forming electrode is composed, in this exemplary embodiment, of a printed circuit trace in the border area 107 between the first and second solid electrolyte layer 105, 106, of a further printed circuit trace in the region of the through-hole plating 110, and of a first contact area 111, connected to the supply lead 100 of the signal-forming electrode and situated on an outside surface of the sensor element. In the region of the through-hole plating 110, the supply lead 100 of the signal-forming electrode proceeds from the border area 107 through the first solid electrolyte layer 105 to the first contact area 111. The shielding 101 likewise proceeds to a second area 112. The positioning shown in FIG. 3 of the supply lead of the signal-forming electrode, the first insulating layer 103, the shielding 101 and the second insulating layer 104 is continued in the region of the through-hole plating 110. After that, in the region of the through-hole plating 110, the supply lead 100 of the signal-forming electrode is surrounded, at least as far as possible by the shielding 101, the supply lead 100 of the signal-forming electrode and the shielding 101 being separated by a first insulating layer 103, and the second insulating layer 104 separating the shielding 101 from the first and second solid electrolyte layers 105, 106. The through-hole plating is put into the first solid electrolyte layer 105, using a method known to one skilled in the art.

Figure 5:
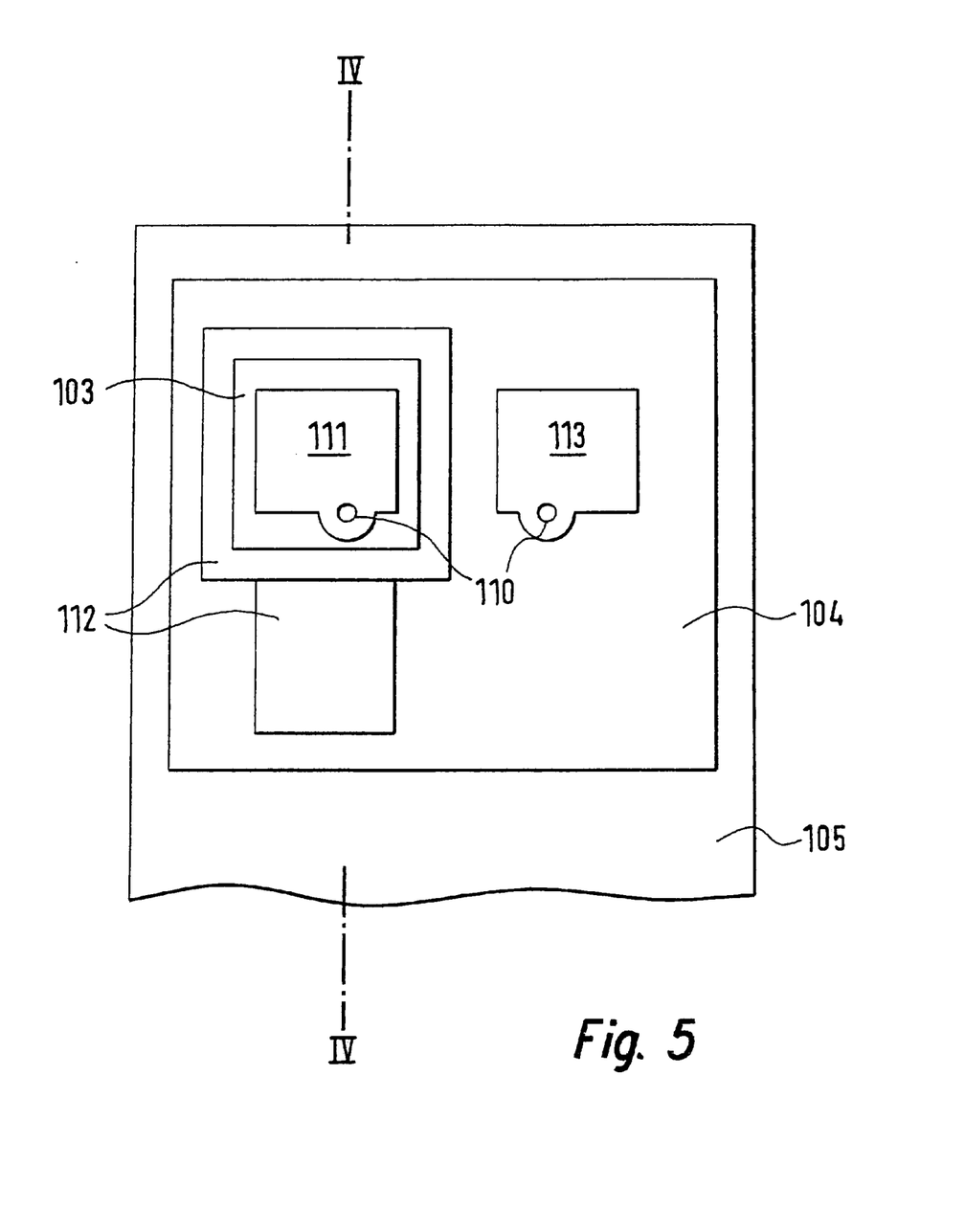
FIG. 5 shows a top view of the sensor element according to the present invention in the region of the connecting side.

FIG. 5 shows a connecting-side section of the large surface of the first solid electrolyte layer 105, the second insulating layer 104, the second contact area 112, the first insulating layer 103 and the contact layer 111 in a top view. Furthermore, a third contact area 113, electrically connected to electrical element 102 by through-hole plating 110, is affixed to the large area of the insulating body 105. The second contact area 112 is affixed to the outer surface of the solid electrolyte layer 105 in such a way, that fault currents which flow because of impurities on the outer surface of the first solid electrolyte layer 105, at a sufficiently large potential difference between the first contact area 111 and the third contact area 113, are absorbed by the second contact area 112, so that the currents in supply lead 100 of the signal-forming electrode which are used for determining the concentration of the exhaust gas, cannot be corrupted by fault currents.

In case the supply lead of the signal-forming electrode is positioned in the border area 107 between a first and a second solid electrolyte layer 105, 106, and the fault currents flow essentially in the border area 107, it may also be sufficient if the shielding 101 at least almost completely surrounds the supply lead 100 of the signal-forming electrode in the border area 107.

It is conceivable that the shielding 101 could be made as a continuous layer or as a sufficiently fine-meshed net. Additionally, an embodiment of the present invention is conceivable, in which the second insulating layer 104 is omitted. It is equally conceivable that another insulating body could be provided instead of at least one solid electrolyte layer 105, 106.

Beyond that, it is also conceivable that the signal-forming electrode could be surrounded by a shielding 101 at least regionally, as long as the designated function of the signal-forming electrode is not disturbed by the shielding 101. Thus, for example, the shielding could shield the signal-forming electrode from the electrical element in such a way, that a contact of the electrode, making possible the functioning of the electrode, for example, with a solid electrolyte layer and/or with a gas chamber is present.

Figure 6:
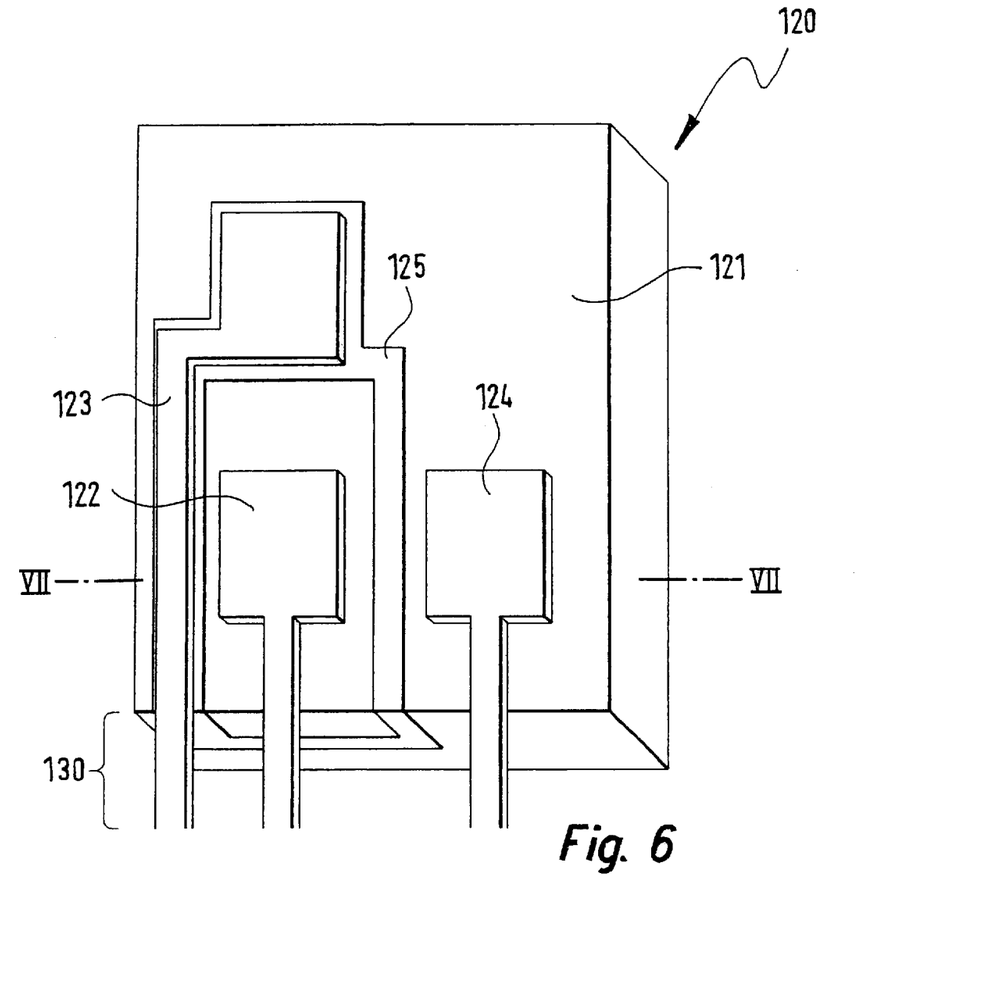
FIG. 6 shows a perspective representation of a bonding device provided for a sensor element.
Figure 7:
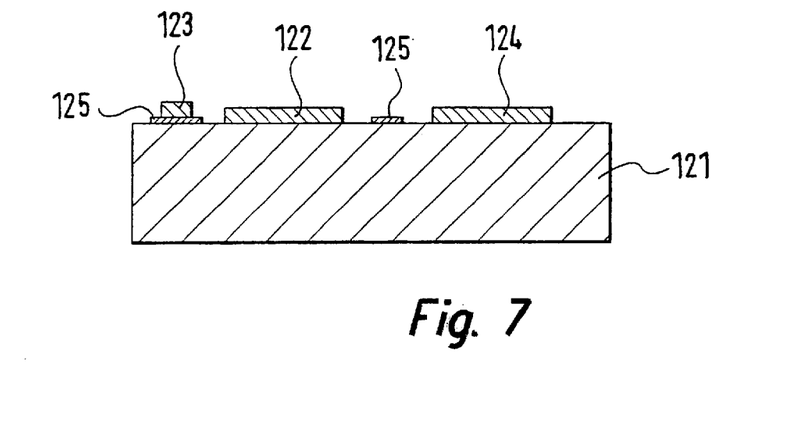
FIG. 7 shows a section through the bonding device along line VII—VII in FIG. 6.

FIG. 6 and FIG. 7 show a bonding device 120 which establishes a connection between contact areas 111, 112, 113 of sensor element 114 and a cable conducting the signals out of the sensor, which is not shown in greater detail. For this purpose, a first conductor element 122 for the signal-forming electrode, a second conductor element 123 for the shielding, and a third conductor element 124 for the electrical element are affixed to the carrier 121. The conductor elements 122, 123, 124 are, for example, stable metal strips which are fastened in a suitable way, for instance, on the ceramic carrier 121. The bonding device 120 is brought into contact with sensor element 114 in such a way that conductor elements 122, 123, 124 are in electrical contact with respective contact areas 111, 112, 113. In the cable-side region 130 the conductor elements are brought out of the sensor in the form of cable, for example, in a manner known to one skilled in the art. On the carrier 121 there is also affixed a shielding printed circuit trace 125 which is in contact with the second conductor element 123 and completely surrounds the first conductor element 122 on the surface of the carrier 121. This achieves that fault currents which flow, for example, for reasons of impurities on the surface of carrier 121, at a sufficiently large potential difference between the first conductor element 122 and the third conductor element 124, are completely absorbed by shielding printed circuit trace 125.

Thus, the exemplary embodiments of the present invention illustrated in FIGS. 3 through 7 ensure that both with sensor element 114 and bonding device 120 the supply lead 100 of the signal-forming electrode or the first conductor element 122, as a rule, is surrounded by shielding 101 or shielding printed circuit trace 125, respectively, in such a way that only small or no fault currents can flow between the electrical element 102 and the supply lead 100 of the signal-forming electrode or the first conductor element 122. What is also conceivable is providing the arrangement according to the present invention, with regard to shielding, only regionally in the sensor element 114 and/or in bonding device 120.

Yet another exemplary embodiment of the present invention is conceivable, in which, with regard to sensor element 114, not the supply lead 100 of the signal-forming electrode but rather the electrical element, e.g. the heater 24, 64 of the sensor element 10, 50 is surrounded at least regionally by a shielding, and with regard to the bonding device 120, not the first conductor element 122 but rather the third conductor element is surrounded at least regionally by a shielding printed circuit trace. The measures described in FIGS. 3 through 7 concerning the first named exemplary embodiments can simply be transferred to this further exemplary embodiment by one skilled in the art.

In the sense of the present invention, a signal-forming electrode is understood to mean any electrode whose function is impaired by taking on fault currents. Thus, for example, a signal-forming electrode can also be taken to mean a reference electrode which, because of the external wiring, pumps a reference gas into an internal reference gas chamber. The pumping into the internal reference gas chamber, and therefore the signal formation in the sensor element, are adversely affected by fault currents into this reference electrode, or rather its supply lead.

In the probes described in FIGS. 1 and 2, during operation, the electrodes and the heater are given defined potentials by an external wiring not illustrated in greater detail. Because of the external wiring customary with the broadband lambda probe (FIG. 1) a large potential difference appears, for example, between the heater 24 or rather the heater supply leads 28 and the supply lead 42 of the signal-forming external pump electrode 41. Thus, the external pump electrode 41 is typically at a potential of approximately 1.5 volt and 4 volt, while one of the heater supply leads 28 is at a potential, interchangeably, of 0 and 13 volt. As opposed to this, the internal pump electrode 34 is typically at a potential of approximately 2.5 volt, the currents flowing in the internal pump electrode 34 having no influence on the determination of the measuring gas concentration. Thus, the external pump electrode supply lead 42 corresponds to the supply lead 100 of the signal-forming electrode. The internal pump electrode supply lead 35 corresponds to the shielding 101 or is short-circuited with the shielding 101, and the heater 24 and the heater supply leads 28 with the electrical element 102.

If the broadband lambda probe is operated according to the arrangement described in FIGS. 3 to 5, the fault currents into the outer pump electrode supply lead 42 decrease considerably, since the potential difference between outer pump electrode 41 and inner pump electrode 34 is substantially lower than that between outer pump electrode 41 and heater 34 or heater supply lead 28, respectively. Since the inner pump electrode 34 is, furthermore, at a constant potential, the still remaining low fault current is constant, and therefore easy to correct, or rather, it changes at the most with the variable potential of outer pump electrode 41.

Because of the usual outer wiring of the NOx sensor illustrated in FIG. 2, the signal-forming NOx pump electrode 72 is at a potential of about 2.5 volt, just as the third oxygen pump electrode 79, currents flowing in the third oxygen pump electrode 79 having no influence on the determination of the measuring gas concentration. The reference electrode 67 is at a potential of approximately 3 volt. The first and the second oxygen pump electrode 70, 77 are short-circuited, and are at a potential of about 2.3 volt. The oxygen outer pump electrode 60 is at changing potentials between 0 and 5 volt. One of the heater supply leads 58 is at a potential of alternately 0 volt and 13 volt. And so, a large potential difference appears between the signal-forming NOx pump electrode 72 and the heater 64, or rather the heater supply lead 58, and also between NOx pump electrode 72 and the oxygen outer pump electrode 60, which can lead to fault currents into the supply lead of the NOx pump electrode 73. Such a potential difference can equally appear between the NOx pump electrode 72 and reference electrode 67 or the NOx pump electrode 72 and the first or second oxygen pump electrode 70, 77, respectively. When the NOx sensor in the arrangement described in FIGS. 3 to 5 is operated, the supply lead 100 of the signal-forming electrode corresponds to the supply lead of the NOx pump electrode 73, and electrical element 102 corresponds to heater 64 or rather the heater supply lead 58, to the first and second oxygen pump electrode 70, 77 or rather their supply leads 71, 78, to the oxygen outer electrode 60 or rather its supply lead 61, or to reference electrode 67 or rather its supply lead 68. The shielding 101 corresponds to the supply lead of the third oxygen pump electrode 80 or is short-circuited with the supply lead of the third oxygen pump electrode 80. Since, therefore, the supply lead 100 of the signal-forming electrode and the shielding 101 are at the same potential, the fault currents are completely absorbed by the shielding 101.

What is claimed is:

1. An electrochemical measuring sensor for determining at least one of a gas component and a gas concentration in a gas mixture, comprising:

a sensor element including at least one signal-forming electrode having a supply lead;

at least one electrical element having an electrical potential that differs from an electrical potential of the at least one signal-forming electrode; and an electrically conducting shielding at least regionally surrounding the supply lead of the at least one signal-forming electrode such that fault currents appearing because of a potential difference between the supply lead of the at least one signal-forming electrode and the at least one electrical element flow at least predominantly between the at least one electrical element and the electrically conducting shielding.

2. The measuring sensor according to claim 1, wherein: the electrically conducting shielding is at an electrical potential lying at least close to an electrical potential of the supply lead of the at least one signal-forming electrode.

3. The measuring sensor according to claim 1, wherein: the electrically conducting shielding is at an at least nearly constant electrical potential.

4. The measuring sensor according to claim 1, further comprising:
a first insulating layer that separates the electrically conducting shielding from the supply lead of the at least one signal-forming electrode.

5. The measuring sensor according to claim 1, further comprising:
a further electrode that short-circuits the electrically conducting shielding and that has an electrical potential that is at least close to an electrical potential of the supply lead of the at least one signal-forming electrode.

6. The measuring sensor according to claim 5, wherein: the supply lead of the at least one signal-forming electrode includes an outer pump electrode supply lead, the further electrode includes an inner pump electrode, and
the at least one electrical element includes at least one of a reference electrode, a reference electrode supply lead, a heater, and a heater supply lead in a broadband lambda sensor.

7. The measuring sensor according to claim 5, wherein: supply lead of the at least one signal-forming electrode includes a supply lead of a NOx pump electrode, the further electrode includes a third oxygen pump electrode, and
the at least one electrical element includes at least one of an oxygen outer pump electrode, a reference electrode, a first oxygen pump electrode, a second oxygen pump electrode, a heater, a supply lead of the oxygen outer pump electrode, a supply lead of the reference electrode, a supply lead of the first oxygen pump electrode, a supply lead of the second oxygen pump electrode, and a supply lead of the heater in a NOx sensor.

8. The measuring sensor according to claim 5, wherein: the electrically conducting shielding is made of the same material as the further electrode.

9. The measuring sensor according to claim 5, wherein: the electrically conducting shielding includes a supply lead of the further electrode.

10. The measuring sensor according to claim 1, further comprising:
an insulating body; and
a further insulating body, wherein:
the supply lead of the at least one signal-forming electrode and the electrically conducting shielding are arranged between the insulating body and the further insulating body, and
the supply lead of the at least one signal-forming electrode is at least nearly completely jacketed on all sides by the electrically conducting shielding.

11. The measuring sensor according to claim 1, further comprising:
an insulating body on a surface of which is mounted the supply lead of the at least one signal-forming electrode, wherein:
the surface of the insulating body otherwise borders on a gas chamber,
the electrically conducting shielding is mounted on the surface of the insulating body, and
the electrically conducting shielding at least almost completely surrounds the supply lead of the at least one signal-forming electrode in a border plane between the insulating body and the gas chamber.

12. The measuring sensor according to claim 1, further comprising:
a first insulating body; and
a second insulating body, wherein:
the supply lead of the at least one signal-forming electrode is mounted in a border plane between the first insulating body and the second insulating body,
the electrically conducting shielding is mounted in the border plane, and
the electrically conducting shielding at least nearly completely surrounds the supply lead of the at least one signal-forming electrode in the border plane.

13. The measuring sensor according to claim 1, wherein: the electrically conducting shielding includes a continuous layer.

14. The measuring sensor according to claim 1, wherein: the electrically conducting shielding includes a sufficiently fine-meshed net.

15. The measuring sensor according to claim 1, further comprising:
a first insulating body;
a second insulating body; and
an insulating layer, wherein:
the electrically conducting shielding is separated from at least one of the first insulating body and the second insulating body, bordering on the electrically conducting shielding, by the insulating layer.

16. The measuring sensor according to claim 1, wherein: the at least one signal-forming electrode is also at least regionally surrounded by the electrically conducting shielding.

17. An electrochemical measuring sensor for determining at least one of a gas component and a gas concentration in a gas mixture, comprising:
a sensor element including at least one signal-forming electrode having a supply lead;
at least one electrical element having an electrical potential that differs from an electrical potential of the at least one signal-forming electrode; and
an electrically conducting shielding at least regionally surrounding the at least one electrical element such that fault currents appearing because of a potential difference between the supply lead of the at least one signal-forming electrode and the at least one electrical element flow at least predominantly between the at least one electrical element and the electrically conducting shielding.

18. The measuring sensor according to claim 17, wherein: the electrically conducting shielding is at an electrical potential lying at least close to an electrical potential of the supply lead of the at least one signal-forming electrode.

19. The measuring sensor according to claim 17, wherein: the electrically conducting shielding is at an at least nearly constant electrical potential.

20. The measuring sensor according to claim 17, further comprising:
a first insulating layer separating the electrically conducting shielding from the at least one electrical element.

21. The measuring sensor according to claim 17, further comprising:
a further electrode having an electrical potential that is at least close to an electrical potential of the supply lead of the at least one signal-forming electrode, wherein:
the electrically conducting shielding is short-circuited with the further electrode.

22. The measuring sensor according to claim 21, wherein:
the electrically conducting shielding includes a supply lead of the further electrode.

23. The measuring sensor according to claim 21, wherein:
the electrically conducting shielding is made of the same material as the further electrode.

24. The measuring sensor according to claim 17, further comprising:
an insulating body; and
a further insulating body, wherein:
the at least one electrical element and the electrically conducting shielding are arranged between the insulating body and the further insulating body, and
the at least one electrical element is at least nearly completely jacketed by the electrically conducting shielding on all sides.

25. The measuring sensor according to claim 17, further comprising:
an insulating body including a surface on which the at least one electrical element is mounted, wherein:
the surface of the insulating body otherwise borders on a gas chamber,
the electrically conducting shielding is mounted on the surface of the insulating body, and
the electrically conducting shielding at least almost completely surrounds the at least one electrical element in a border plane between the insulating body and the gas chamber.

26. The measuring sensor according to claim 17, further comprising:
an insulating body; and
a further insulating body, wherein:
the at least one electrical element is mounted in a border plane between the insulating body and the further insulating body, and
the electrically conducting shielding is mounted in the border plane, and
the electrically conducting shielding surrounds the at least one electrical element in the border plane at least nearly completely.

27. The measuring sensor according to claim 17, wherein:
the electrically conducting shielding includes a continuous layer.

28. The measuring sensor according to claim 17, wherein:
the electrically conducting shielding includes a sufficiently fine-meshed net.

29. An electrochemical measuring sensor for determining at least one of gas component and a gas concentration in a gas mixture, comprising:
a sensor element including at least one signal-forming electrode having a supply lead;
at least one electrical element having an electrical potential that differs from an electrical potential of the at least one signal-forming electrode;
a first conductor element;
a further conductor element;
at least one cable;
an electrically conducting shielding printed circuit trace; and
a bonding device that electrically connects the at least one signal-forming electrode via the first conductor element and the at least one electrical element via the further conductor element to the at least one cable, wherein:
the first conductor element is connected to the supply lead of the at least one signal-forming electrode, and the first conductor element is surrounded at least regionally by the electrically conducting shielding printed circuit trace such that fault currents appearing because of a potential difference between the first conductor element and the further conductor element flow at least predominantly between the further conductor element and the electrically conducting shielding printed circuit trace.

30. The measuring sensor according to claim 29, wherein:
the electrically conducting shielding printed circuit trace is at an electrical potential lying at least close to an electrical potential of the first conductor element.

31. The measuring sensor according to claim 29, wherein:
the electrically conducting shielding printed circuit trace is at an at least nearly constant electrical potential.

32. The measuring sensor according to claim 29, further comprising:
an electrically conducting shielding; and
a yet another conductor element in contact with the electrically conducting shielding, wherein:
the electrically conducting shielding printed circuit trace is short-circuited with the yet another conductor element.

* * * * *

UNITED STATES PATENT AND TRADEMARK OFFICE
CERTIFICATE OF CORRECTION

PATENT NO. : 6,627,059 B2
DATED : September 30, 2003
INVENTOR(S) : Carsten Springhorn It is certified that error appears in the above-identified patent and that said Letters Patent is hereby corrected as shown below:

Column 3,
Line 38, insert -- The measuring gas reaches the pump chamber, not shown in greater detail in Figure 2, through the measuring gas opening 82, which leads to the outside of sensor element 50. The pump chamber borders on a third and fourth electrode, designated as first and second oxygen pump electrodes 70, 77, whose supply leads 71, 78, in the connecting side region 52, are joined and conducted to a bonding surface 81 via through-hole plating 84. The measuring chamber borders on a fifth electrode designated as Nox pump electrode 72 and a sixth electrode designated as third oxygen pump electrode 79, which are separately conducted, each via its supply lead 73, 80, and each through its through-hole plating 84 to their respective bonding surface 81. --

Signed and Sealed this

Twenty-eighth Day of September, 2004

JON W. DUDAS
*Director of the United States Patent and Trademark Office*